(12) United States Patent
Trevino

(10) Patent No.: US 10,888,673 B2
(45) Date of Patent: Jan. 12, 2021

(54) COUNTERBALANCED NASAL BULB ASPIRATOR

(71) Applicant: Rose Medical Innovations, LLC

(72) Inventor: Reyna Trevino, Naperville, IL (US)

(73) Assignee: Rose Medical Innovations, LLC, Naperville, IL (US)

( * ) Notice: Subject to any disclaimer, the term of this patent is extended or adjusted under 35 U.S.C. 154(b) by 375 days.

(21) Appl. No.: 15/463,013

(22) Filed: Mar. 20, 2017

(65) Prior Publication Data

US 2017/0281881 A1 Oct. 5, 2017

Related U.S. Application Data

(60) Provisional application No. 62/314,507, filed on Mar. 29, 2016.

(51) Int. Cl.
*A61M 11/00* (2006.01)
*A61M 1/00* (2006.01)

(52) U.S. Cl.
CPC ........ *A61M 11/008* (2014.02); *A61M 1/0003* (2013.01); *A61M 1/0072* (2014.02); *A61M 2205/075* (2013.01); *A61M 2209/084* (2013.01); *A61M 2210/0618* (2013.01)

(58) Field of Classification Search
CPC ... A61F 9/0008; A61F 9/0026; A61M 11/008; A61M 1/0003; A61M 1/0072; A61M 2205/075; A61M 2209/084; A61M 2210/0618; A61M 1/0031; A61M 39/24
See application file for complete search history.

(56) References Cited

U.S. PATENT DOCUMENTS

| | | | |
|---|---|---|---|
| 1,481,008 A | 1/1924 | Hodlick | |
| 1,762,237 A | 6/1930 | Moore | |
| 2,890,699 A | 6/1959 | Miller | |
| 4,002,168 A * | 1/1977 | Petterson | A61F 9/0008 222/421 |
| 4,487,336 A | 12/1984 | Sneider | |
| 5,848,993 A * | 12/1998 | Tanhehco | A61M 1/0011 604/217 |
| 7,959,597 B2 | 6/2011 | Baker et al. | |
| 2008/0154183 A1* | 6/2008 | Baker | A61M 1/0058 604/28 |
| 2011/0139149 A1* | 6/2011 | Cacka | A61H 35/04 128/200.14 |
| 2014/0296793 A1* | 10/2014 | Varney | A61M 1/0003 604/212 |
| 2016/0038339 A1* | 2/2016 | Behan | A61F 9/0026 604/290 |

FOREIGN PATENT DOCUMENTS

EP 2216058 11/2008

* cited by examiner

*Primary Examiner* — Kai H Weng

(57) ABSTRACT

A nasal bulb aspirator that can be sized to fit the needs of infants through adults and is designed to ensure that the tip remains hygienically intact by a one-way valve and a counterbalance system that prevents the tip from touching surrounding surfaces, thereby limiting cross contamination from possibly resistant pathogens.

17 Claims, 4 Drawing Sheets

COUNTERBALANCED NASAL BULB ASPIRATOR

CROSS-REFERENCE TO RELATED APPLICATION

This application claims the benefit of U.S. Provisional Patent Application No. 62/314,507 filed Mar. 29, 2016, which is hereby incorporated by reference in its entirety herein.

BACKGROUND OF THE INVENTION

I. Field of the Invention

The present disclosure relates generally to medical bulb suction devices, and more specifically to a bulb aspirator designed to remain hygienically intact and limit cross contamination.

II. Description of the Prior Art

Parents and their children are often frustrated by, and unsure how, to deal with the common build up of nasal congestion of different viscosities. Indeed, at times, infants and small children are admitted to hospitals because of the great difficulty they have with breathing and potentially interfering with their ability to stay hydrated. On a daily basis, health care providers hear countless stories of sleepless nights, poor eating habits, and behavior changes attributed to simple nasal discharge. Most commonly this nasal mucus drainage makes it extremely difficult to eat, drink, and most importantly to tired parents, sleep. More importantly, if this drainage is not removed in a timely manner, it may result in sinusitis as well as ear and chest infections.

At the present time, there are not too many options available for parents and health care providers alike. Cold medications and some holistic care are not Food and Drug Administration approved for infants and toddlers, and in any event are of questionable efficacy.

It is common practice for medical practitioners to find themselves repeating to parents that they need to apply saline and then manual suction as the main regimen for the common cold. For lack of a simple, effective, and more hygienic solutions in the market, medical practitioners may even recommend solutions that they know to be less hygienic and driven by desperation and immediate need of the patients. One such concept is the mechanical aspiration device using parental inspiratory force to aspirate a nose of a child. In addition to being repugnant in concept, as is often mentioned in consumer polls, the nature of these devices can lead to inadvertent contamination of the parents and eventually others in the household.

The most commonly used option is the basic hospital bulb suction device. Unfortunately, this device has many inadequacies. For example, this method of bulb suctioning passages commonly result in physical struggles between the parent and the child, often exacerbated by the nasal discomfort that the bulb causes, in addition to the natural urge of infants to resist restraint, further complicating the procedure. During that struggle, the person attempting to apply the suction may find themselves putting the device down to better control the infant or child, potentially contaminating the suction device with restraint bacteria such as a community acquired methicillin resistant staphylococcus infection (MRSA) or other secondary pathogens. Additionally, it is well known that the basic bulbs can build up pathogens internally in the bulb. Whether internal or secondary, such pathogens are routinely introduced into the nasal passages by the user. Furthermore, if the bulb is not used correctly, whether clean or not, damaged nasal passages are a common outcome.

The present disclosure overcomes these and other problems associated with the current state of the art of nasal aspirators. Accordingly, it is a general object of this disclosure to provide an improved bulb aspirator for aspirating and removing mucus from the nasal and sinus cavities.

It is another general object of the present disclosure to provide a simple, hygienic device for quick and easy mucus removal.

It is a more specific object of the present disclosure to provide a flexible nasal bulb aspirator that provides suction and hygienic collection of mucus without reintroducing the mucus into the child or adult upon repeat suctioning.

It is another more specific object of the present disclosure to provide an ergonomic silicon nozzle that is appropriate for a nose of an infant or child and is transparent enough to visualize the suctioning of secretions.

It is another more specific object of the present disclosure to provide a nasal bulb aspirator having a neck containing a one-way valve and a body containing a one-way valve that in combination permits air to be expelled from the bulb body to create suction to allow the mucus to be drawn in through the nozzle.

It is yet another more specific object of the present disclosure to provide a bulb that is shaped and weighted so as to balance it in a state of equilibrium, keeping the tip upright and away from other surfaces.

Yet another more specific object of the present disclosure is to provide a bulb constructed of three separable pieces and of a material that can be safely placed in a dishwasher and/or boiled for easy hygienic cleaning.

These and other objects, features and advantages of this disclosure will be clearly understood through a consideration of the following detailed description.

SUMMARY OF THE INVENTION

According to an embodiment of the present disclosure, there is provided a nasal aspirator that is supported on an underlying support surface including a bulb, a nozzle with a tip, a one-way valve for permitting air to pass from the tip to the bulb and a one-way valve permitting air to escape from the bulb. A support member balances the bulb aspirator upon the support surface keeping the tip away from the surface.

According to another embodiment of the present disclosure, there is provided counterbalanced nasal bulb aspirator oriented on an underlying support surface including a resilient bulb, a nozzle with a tip for suction of liquids by a vacuum created from compressing and then releasing the bulb, a one-way valve for permitting air to pass from the tip to the bulb and a one-way valve permitting air to escape from the bulb. A support member balances the bulb aspirator upon the support surface keeping the tip away from the surface.

According to another embodiment of the present disclosure, there is provided a bulb aspirator supported on an underlying support surface including a resilient bulb, a nozzle having a tip for suction of liquids by a vacuum created by compressing and then releasing the bulb, and a support member for balancing the bulb aspirator upon the surface to keep the tip away therefrom.

BRIEF DESCRIPTION OF THE DRAWINGS

The present disclosure will be more fully understood by reference to the following detailed description of one or more preferred embodiments when read in conjunction with the accompanying drawings, in which like reference characters refer to like parts throughout the views and in which.

DESCRIPTION OF THE PREFERRED EMBODIMENTS

One or more embodiments of the subject disclosure will now be described with the aid of numerous drawings. Unless otherwise indicated, use of specific terms will be understood to include multiple versions and forms thereof.

Figure 1:
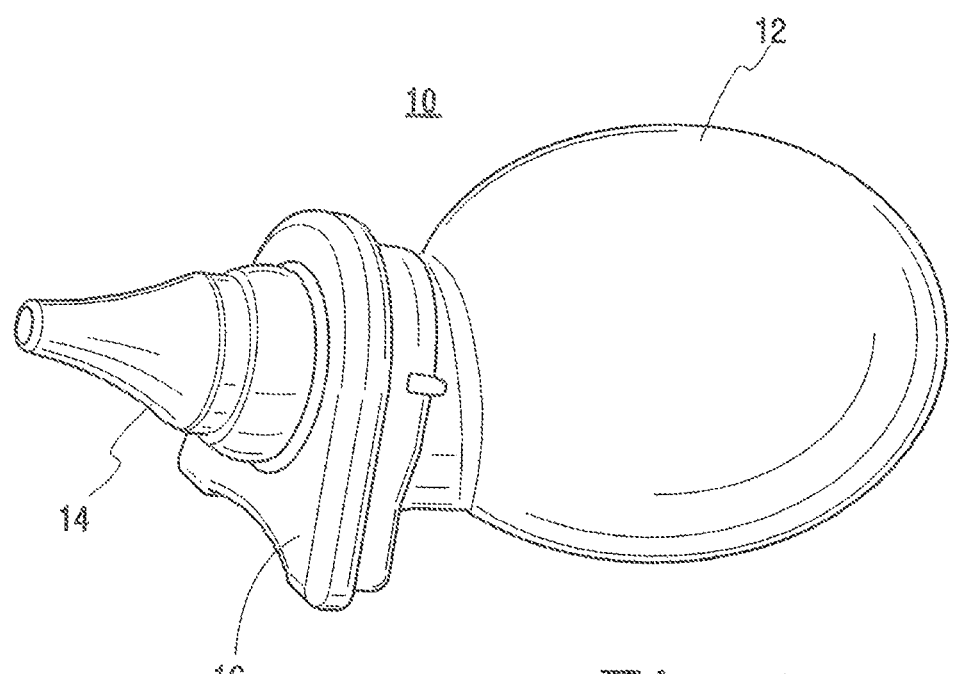
FIG. 1 is a perspective view of a counterbalanced nasal bulb aspirator according to the principles of an embodiment of the present disclosure.
Figure 2:
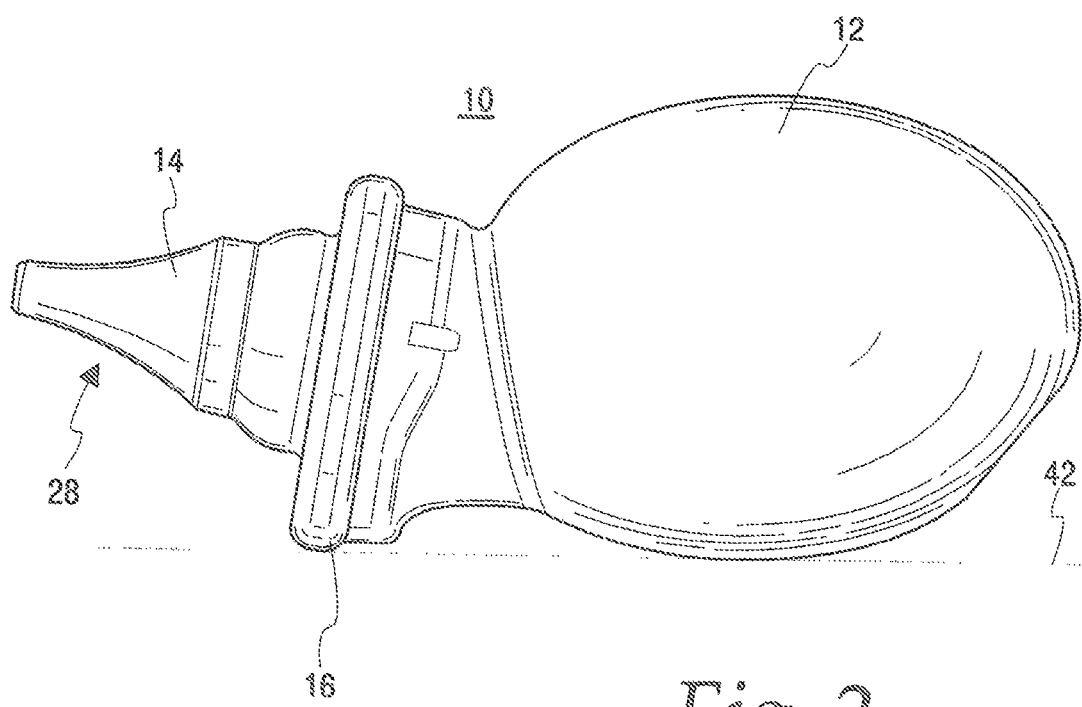
FIG. 2 is a side view of the aspirator of FIG. 1.
Figure 3:
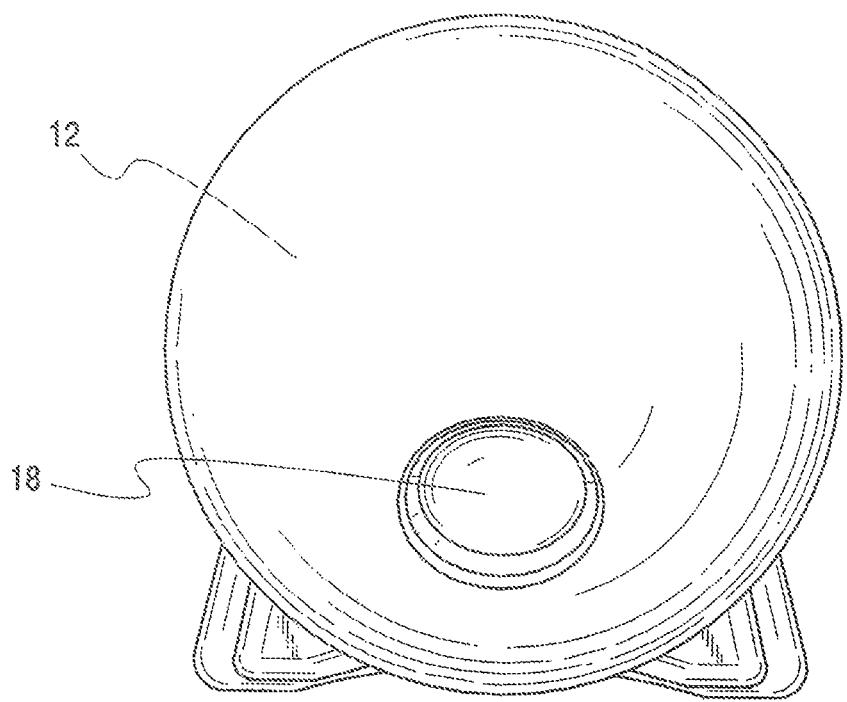
FIG. 3 is a rear view of the aspirator of FIG. 1.
Figure 4:
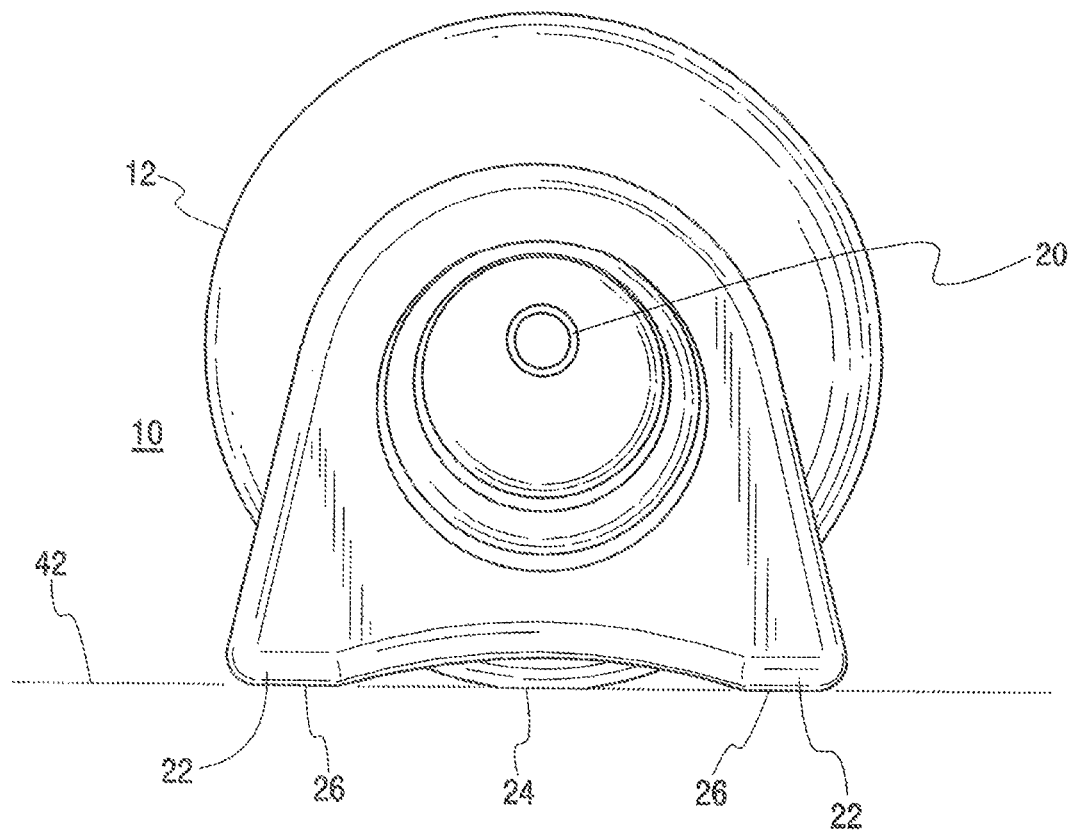
FIG. 4 is a frontal view of the aspirator of FIG. 1.

In any event, turning now to the Figures, and in particular FIGS. 1 and 2, an embodiment of the counterbalanced nasal bulb aspirator 10 of the present disclosure is shown. The main component parts include the bulb 12, the nozzle 14 and the aspirator support member 16. FIGS. 3 and 4 better illustrate additional component parts, including the bulb valve cover 18, the nozzle tip 20 and the legs 22 of the support member 16. While FIG. 5 best shows the contact points of the aspirator with a support surface, and specifically the flattened contact surface 24 on the underside of the bulb 12 and the contact surface 26 of the support member 16 legs 22.

The bulb 12 is made of a resilient, compressible and elastic material that will tend to return to its original shape and produce suction after it has been collapsed. The nozzle tip 20 is made of a pliable material to avoid damaging the mucosal membrane inside the nose. The nozzle may also be conical 28 or have a stepwise widening (see FIG. 2) of the outer diameter to avoid the stem being inserted too deep into the nostril.

During use, the bulb 12 is compressed and the nozzle tip 20 is inserted into a nostril or mouth. The nozzle 14 and the bulb 12 may be made of a single piece or they may be separable for cleaning and maintenance purposes. In any event, there remains an air-tight connection therebetween so that the vacuum created therein by the suction bulb 12 will be transmitted to the hollow tip 20 and produce the desired suction in the tip 20. The compressed bulb 12 is then gradually released to withdraw mucus and secretions from the nostril or mouth. The sucking force is controlled by the user by simply controlling the compressive forces at the bulb.

Figure 6:
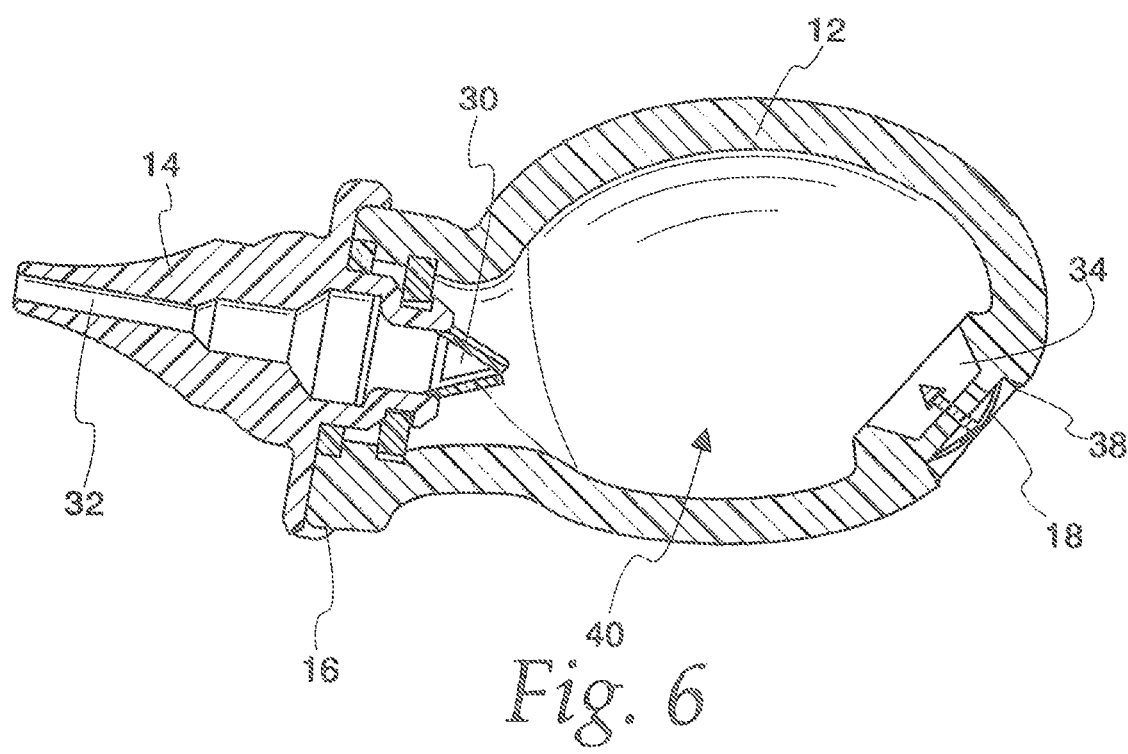
FIG. 6 is a side cross-sectional view of the aspirator of FIG. 1.
Figure 7:
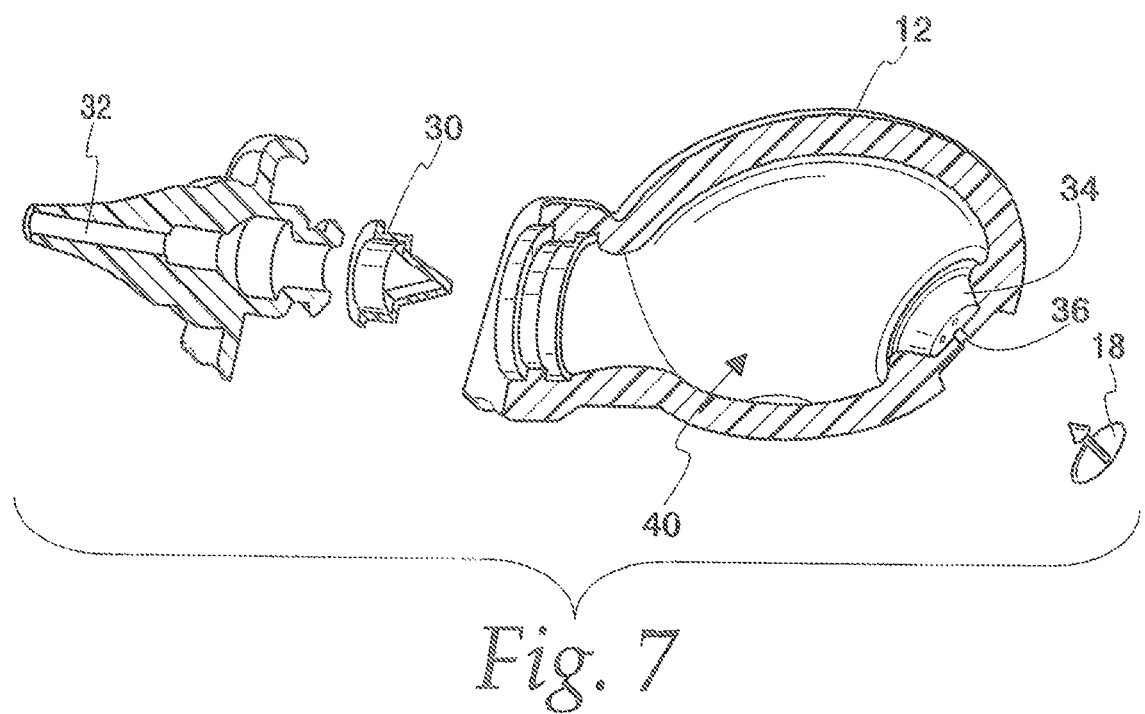
FIG. 7 is a side exploded and cross-sectional view of the component parts of the aspirator of FIG. 1.
Figure 8:
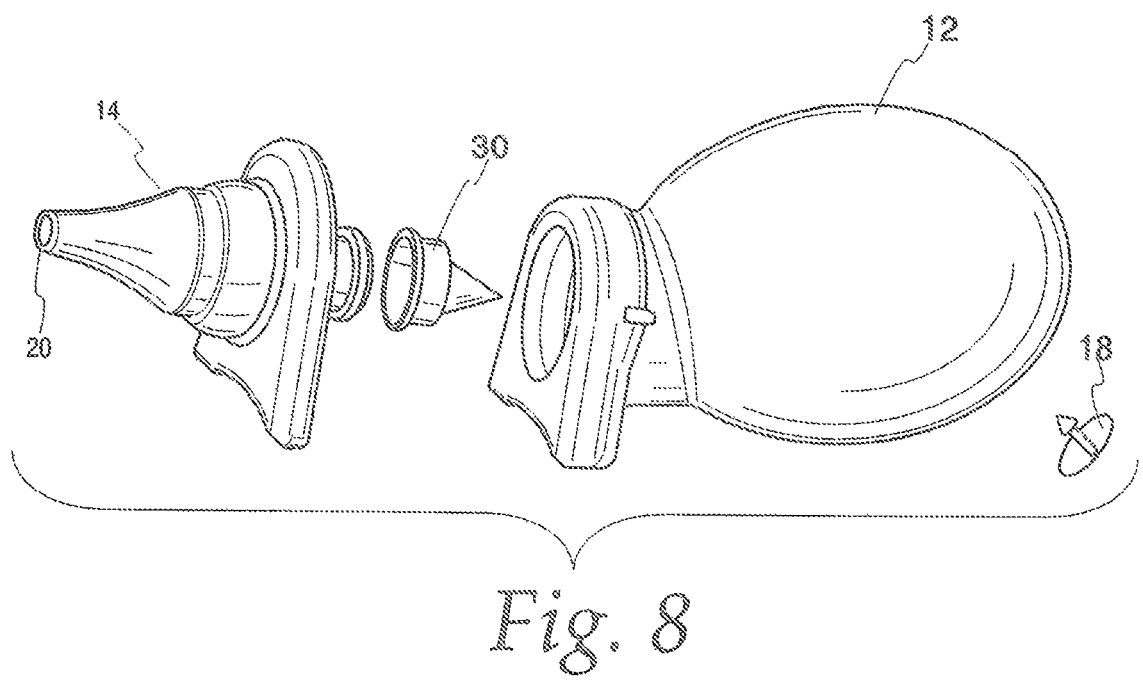
FIG. 8 is a perspective exploded view of the component parts of the aspirator of FIG. 1.

Turning now to the cross-sectional and exploded views of FIGS. 6-8, additional particular features of the present disclosure can now be better described. First, and in order to prevent any positive or forward pressure being created in the tip 20, the bulb 12 is fitted with a first one-way valve 30 (so-called duckbill valve) which permits air to pass from the air passage assembly 32 within the nozzle into the bulb 12, but positively prevents any reverse flow from the bulb 12 into the assembly 32 and ultimately out of the tip 20 and into a nostril or mouth.

Similarly, the rear of the bulb 12 includes a second one-way valve 34 for permitting air to escape from the bulb 12 when the bulb 12 is collapsed. This valve 34 includes an aperture 36 in the bulb 12 which is covered by a thin rubber flap 18 of preferably silicon. The flap 18 is attached at one side to the valve insert 38 while the other side of the flap is left free so as to permit a flap valve action to obtain this so-called umbrella valve.

Accordingly, and during use, the bulb 12 is compressed and the first one-way valve 30 is tightly closed to prevent positive pressure from being built up within the air passage assembly while the aperture 36 is uncovered by the flap 18 to permit the air in the bulb to be expelled therefrom as the bulb is compressed. When the pressure on the bulb 12 is relaxed, the flap 18 will tightly close the aperture 36 and air will be drawn into the bulb 12 through the first one-way valve 30, thereby creating a suction in the bulb collection chamber 40. This suction will be transmitted to the tip 20 of the nozzle 14 and cause any mucus or other secretions in the nostril or mouth to be drawn into the collecting chamber 40. The bulb and/or nozzle may be of a viewable clear, blow molded acrylic with flanges at either end to create an airtight seal to both the tip and the bulb.

Figure 5:
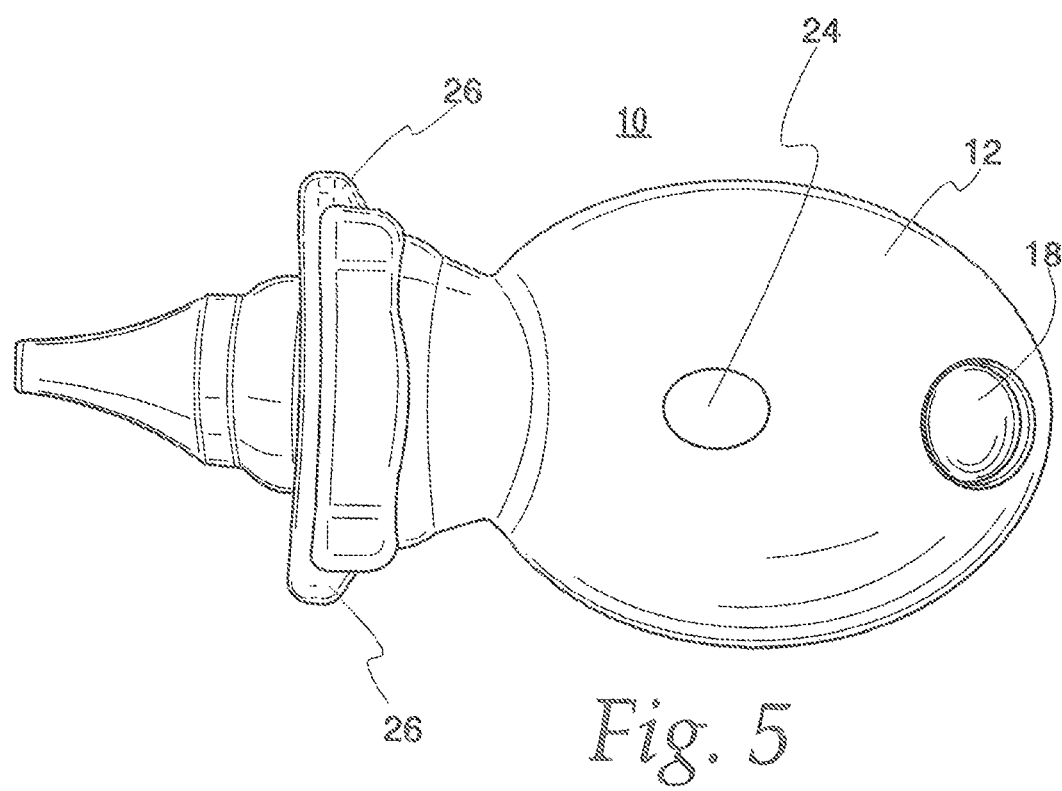
FIG. 5 is a bottom plan view of the aspirator of FIG. 1.

The counterbalance system of the present disclosure includes the support member 16 as well as the flattened contact surface 24 of the bulb. As such, the system of the nasal bulb aspirator 10 prevents the tip 20 from touching surrounding surfaces, thereby limiting cross contamination from possibly resistant pathogens. As best shown in FIG. 4, the bulb aspirator 10 is properly oriented upon a support surface 42 when the contact surfaces 26 of the weighted support legs 22 and the flattened contact surface 24 of the underside of the bulb 12 rest upon the underlying support surface 42. This keeps the tip isolated and remote from the support surface. Again, as shown in FIGS. 2, 4 and 5 (shown best in 4), the support member and flattened underside together isolate the tip. It is this concurrent/simultaneous support of the contact points that keep the tip upright and therefore minimizing any potential cross contamination.

The bulb aspirator 10 is preferably injection molded to maintain the necessary geometry in the design and to add the proper weight to the feet 22 with a more condensed silicone. The bulb is molded from medical grade silicone that is lightweight with release recoil to assist in creating the negative pressure that is optimal for suctioning. The aspirator tip 20 is injection molded medical grade silicone for a softer touch, durability and machine-washability. In that regard, all components may be separable for cleaning and maintenance purposes. All components may be dishwasher safe and capable of sustaining boiling temperatures. The valves are preferably removable or replaceable if damaged or overused.

The foregoing detailed description has been given for clearness of understanding only and no unnecessary limitations should be understood therefrom. Accordingly, while one or more particular embodiments of the disclosure have been shown and described, it will be apparent to those skilled in the art that changes and modifications may be made therein without departing from the invention if its broader aspects, and, therefore, the aim in the appended claims is to cover all such changes and modifications as fall within the true spirit and scope of the present disclosure.

What is claimed is:

1. A nasal aspirator supported on an underlying support surface, the aspirator comprising:
    a resilient bulb having a resting state and a compressed state said bulb having an underside having a flattened surface for balancing said bulb upon said underlying support surface;
    a nozzle having a tip;
    a first one-way valve for permitting air to pass from said tip into said bulb when said bulb is released from said compressed state to aspirate a nasal passage;
    a second one-way valve for permitting air to escape said bulb during compression; and
    a support member disposed about a neck portion of said aspirator extends to form one or more legs for balancing said bulb upon said underlying support surface whereby said flattened surface of said bulb and said one or more legs concurrently isolate said tip from said underlying support surface when said aspirator is not in use.

2. The aspirator as defined in claim 1 wherein said support members including at least two legs.

3. The aspirator as defined in claim 2 wherein said legs are weighted.

4. The aspirator as defined in claim 2 wherein said legs including flattened contact surfaces for balancing said bulb upon said underlying support surface.

5. The aspirator as defined in claim 1 wherein said nozzle includes a conical shape.

6. The aspirator as defined in claim 1 wherein said bulb, said nozzle and said first one-way valve are separable.

7. A counterbalanced nasal bulb aspirator oriented on an underlying support surface, the aspirator comprising:
    a resilient bulb having an underside having a flattened surface for balancing said bulb upon said underlying support surface;
    a nozzle having a tip for suction of liquids by a vacuum created by compressing said bulb and thereafter releasing said bulb;
    a first one-way valve for permitting air to pass from said tip into said bulb;
    a second one-way valve for permitting air to escape said bulb; and
    an aspirator support member positioned near a neck portion of said bulb extends to form one or more legs for balancing said bulb upon said underlying support surface whereby said flatten surface of said bulb and said one or more legs together isolate said tip from said underlying support surface when said aspirator is at rest.

8. The aspirator as defined in claim 7 wherein said support members including at least two legs.

9. The aspirator as defined in claim 8 wherein said legs are weighted.

10. The aspirator as defined in claim 8 wherein said legs including flattened contact surfaces for balancing said bulb upon said underlying support surface.

11. The aspirator as defined in claim 7 wherein said nozzle includes a conical shape.

12. The aspirator as defined in claim 7 wherein said bulb, said nozzle and said first one-way valve are separable.

13. A bulb aspirator supported on an underlying support surface, the aspirator comprising:
    a resilient bulb having an underside having a flattened contact surface for balancing said bulb upon said underlying support surface;
    a nozzle having a tip for suction of liquids by a vacuum created by compressing said bulb and thereafter releasing said bulb; and
    an aspirator support member positioned near a neck portion of said bulb extends to form one or more legs for balancing said bulb upon said underlying support surface whereby flattened surface of said bulb and said one or more legs simultaneously isolate said tip from said underlying support surface.

14. The aspirator as defined in claim 13 wherein said support member includes at least two legs.

15. The aspirator as defined in claim 14 wherein said legs are weighted.

16. The aspirator as defined in claim 14 wherein said legs include flattened contact surfaces for balancing said aspirator upon said underlying support surface.

17. The aspirator as defined in claim 13 wherein said nozzle includes a conical shape.

* * * * *